United States Patent

Torii et al.

[11] Patent Number: 5,337,148
[45] Date of Patent: Aug. 9, 1994

[54] APPARATUS FOR MONITORING A GUARD WINDOW OF AN ARC SENSOR

[75] Inventors: Nobutoshi Torii, Hachioji; Ryo Nihei; Hiroshi Wakio, both of Minamitsuru, all of Japan

[73] Assignee: Fanuc, Ltd., Yamanashi, Japan

[21] Appl. No.: 952,501

[22] PCT Filed: Apr. 2, 1992

[86] PCT No.: PCT/JP92/00409

§ 371 Date: Dec. 2, 1992

§ 102(e) Date: Dec. 2, 1992

[87] PCT Pub. No.: WO92/17754

PCT Pub. Date: Oct. 15, 1992

[30] Foreign Application Priority Data

Apr. 2, 1991 [JP] Japan .................................. 398088

[51] Int. Cl.$^5$ .............................. G01J 1/04; B23K 9/10
[52] U.S. Cl. .................................... 356/376; 356/434
[58] Field of Search ............... 356/376, 433, 434, 448

[56] References Cited

U.S. PATENT DOCUMENTS

| 4,486,098 | 12/1984 | Buchegger et al. | 356/448 |
| 4,576,482 | 3/1986 | Pryor | 356/356 |
| 4,826,316 | 5/1989 | Odum . | |

FOREIGN PATENT DOCUMENTS 59-30757 2/1984 Japan .
62-190368 12/1987 Japan .

OTHER PUBLICATIONS

Patent Abstracts of Japan, vol. 15, No. 196, May 21, 1991.
Patent Abstracts of Japan, vol. 012, No. 460, Dec. 5, 1988.
Week 9033, Derwent Publications Ltd., London, Jul. 26, 1990.

Primary Examiner—Richard A. Rosenberger
Attorney, Agent, or Firm—Nikaido, Marmelstein, Murray & Oram

[57] ABSTRACT

The purpose of the invention is to properly determine the replacement time of a guard window of an arc sensor using an original function of the arc sensor.

The apparatus for monitoring a guard window of an arc sensor according to the present invention is provided with an arc sensor guard window (28) mounted on an arc sensor unit (20) and a standard reflecting plate (30) located at a position a determined distance from the front surface of the guard window (28). And the apparatus detects the reflected light (27) from the standard reflecting plate (30) when a laser beam (26) scans the standard reflecting plate (30), before the guard window (28) is used for an arc welding operation. The apparatus memorizes the quantity of detected light reception as the first quantity. The apparatus then detects the reflected light (27) from the standard reflecting plate (30) in the same way as before, after the guard window (28) is used for an arc welding operation. The apparatus memorizes the quantity of detected light reception as the second quantity of detected light reception as the second quantity. Based on the difference between the first quantity and the second quantity, the condition of the guard window (28) is checked and it is determined whether or not the guard window (28) should be replaced.

3 Claims, 4 Drawing Sheets

APPARATUS FOR MONITORING A GUARD WINDOW OF AN ARC SENSOR

TECHNICAL FIELD

The present invention relates to an apparatus for monitoring a guard window of an arc sensor mounted on a welding torch of an arc welding robot, and relates more particularly to an apparatus for monitoring a guard window of an arc sensor, which determines the replacement time of the guard window.

BACKGROUND ART

An arc sensor used for searching a welding line of an arc welding robot and otherwise, is mounted on a welding torch of the robot, and because of this, the arc sensor experiences internal structure damage or accumulates stains on the lens as a result of spatterings and lampblack generated during welding. Therefore the arc sensor is provided with a replaceable guard window to guard the internal structure from spatterings and lampblack.

However, this guard window is sometimes burned black by the spatterings and accumulates stains as a result of lampblack and etc. in proportion to the number of welding operations, so that an incident beam and a reflected beam of a laser beam cannot easily penetrate the window. When penetration of the incident beam and reflected beam through the window becomes difficult, the detecting capability of the arc sensor is reduced and the detecting accuracy of the same is also reduced. Therefore, the guard window is usually replaced at determined intervals or as required, or the stains on the window are wiped clean after discerning the accumulated stains on the window with the naked eye.

However, if the guard window is replaced at determined intervals, stains accumulate and replacement thereof is quite often too late, in the case of a large number of welding operations, and as a result, the detecting capability of the arc sensor is reduced. On the other hand, replacement thereof can be too early, and a window is unnecessarily replaced in the case of a small number of welding operations during the determined interval.

Replacement of the guard window as required is indiscriminate and unreliable depending on individual operators thereof, for instance, by discerning accumulated stains with the naked eye, thereby posing the same problem as the case when the windows are replaced at determined intervals.

DISCLOSURE OF THE INVENTION

Accordingly, it is an object of the present invention to provide an apparatus for monitoring a guard window of an arc sensor, capable of determining the proper replacement time by using an original function of the arc sensor, in the light of the above-mentioned problem.

In order to solve the above-mentioned problem, the apparatus for monitoring the guard window of the arc sensor according to the present invention, which determines the replacement time of the guard window is characterized in that it includes a standard reflecting plate located at a position a determined distance from the front surface of the guard window of the arc sensor; a detecting means that detects a first quantity of light reception from the light reflected when a laser beam scans the standard reflecting plate before the guard window is used for arc welding, and that detects a second quantity of light reception from the light reflected when the laser beam scans the standard reflecting plate after the guard window is used for arc welding; and a judging means to determine the replacement time of the guard window of the arc sensor based on a comparison of the first quantity of light reception and the second quantity of light reception.

First, an unused (brand new) guard window is mounted on an arc sensor, and a standard reflecting plate is then located at the position a determined distance from the front surface of the guard window. The reflected light is detected when the laser beam scans the standard reflecting plate in that state, and data concerning the quantity of light reception is stored in a memory as the first quantity. Then after using the guard window for arc welding operation, the standard reflecting plate is located at a position a determined distance from the front surface of the guard window of the arc sensor. The data concerning the quantity of light reception is stored in a memory as the second quantity, and based on the data of the first and the second quantities of light reception, the condition of the guard window is determined and a decision is made regarding whether the guard window should be replaced or not, thereby providing a suitable replacement time for the guard window of the arc sensor.

BEST MODE FOR CARRYING OUT THE INVENTION

An embodiment of the present invention will be explained hereinafter, referring to the attached drawings.

Figure 1:
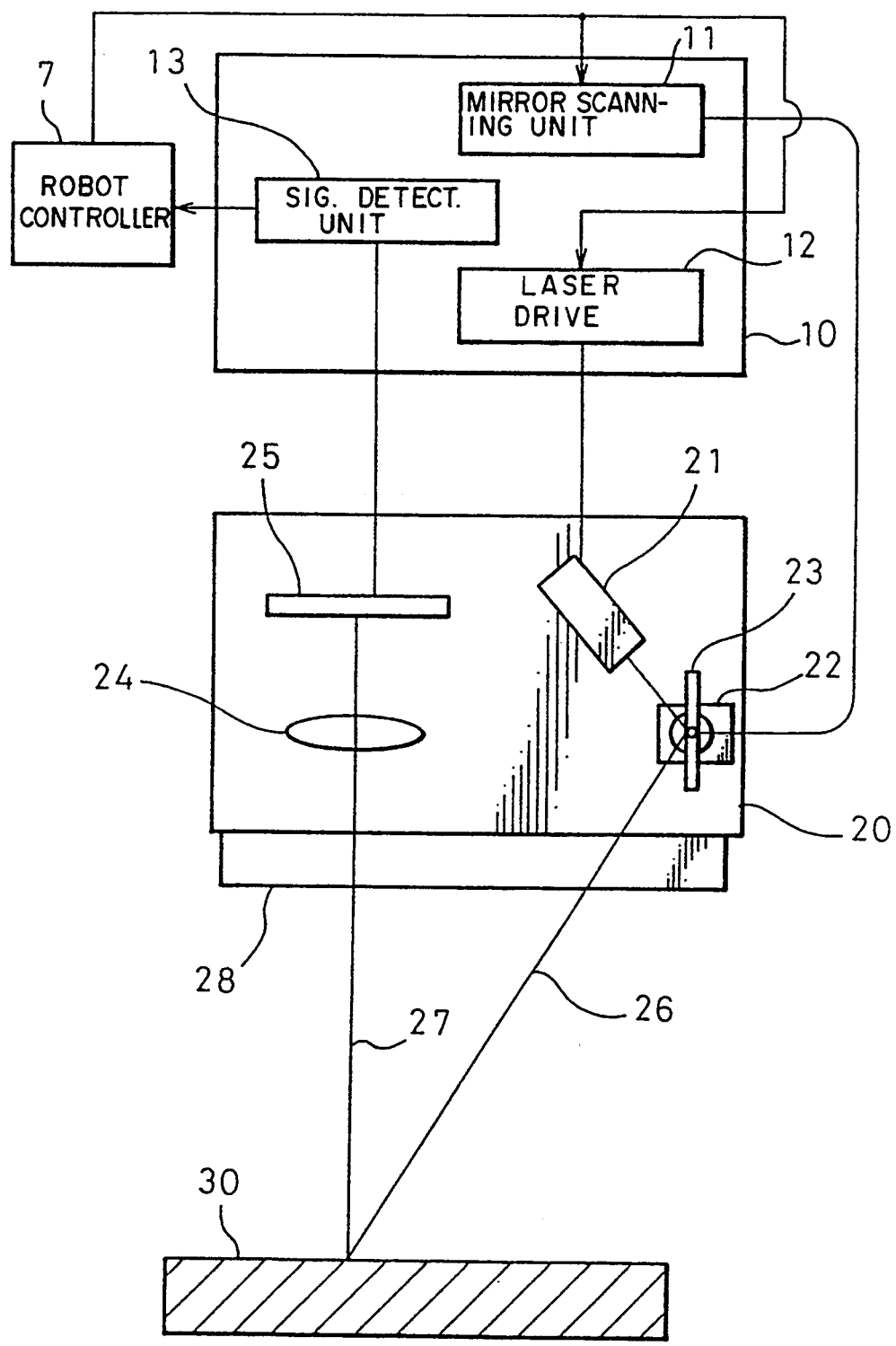
FIG. 1 is a block diagram showing the structure of an apparatus for monitoring a guard window of an arc sensor of the present invention.

FIG. 1 is a block diagram showing a structure of an apparatus for monitoring a guard window of an arc sensor of the present invention. An arc sensor control unit 10 is composed of a mirror scanning unit 11, a laser drive 12 and a signal detecting unit 13. On the other hand, an arc sensor unit 20 is composed of a laser oscillator 21, a scanner 22 and an oscillation mirror 23 oscillated by the scanner 22. The arc sensor unit 20 is also composed of a lens 24 and a light receptive element 25. And, for example, a C.C.D. or a P.S.D. (position sensing device) is used for a light receptive element 25. An arc sensor guard window 28 is also provided on the front surface of the arc sensor unit 20. This arc sensor guard window 28 is, for example, composed of a heat resisting glass or a special resin, and protects internal constitutions of the arc sensor unit 20 from spatterings and lampblack generated during welding operation.

The laser oscillator 21 oscillates after receiving drive power from the laser drive 12 and outputs a laser beam 26. The scanner 22 is driven by a drive current generated from the mirror scanning unit 11 and oscillates the oscillation mirror 23. Generally, the oscillation mirror 23 scans the laser beam 26 onto a work (not shown), and the reflected light is detected by the light receptive element 25. Data detected by the element 25 are sent to a robot controller 7, hereinafter mentioned, via the signal detecting unit 13. The robot controller 7 detects a welded point of the work based on the data.

Figure 2:
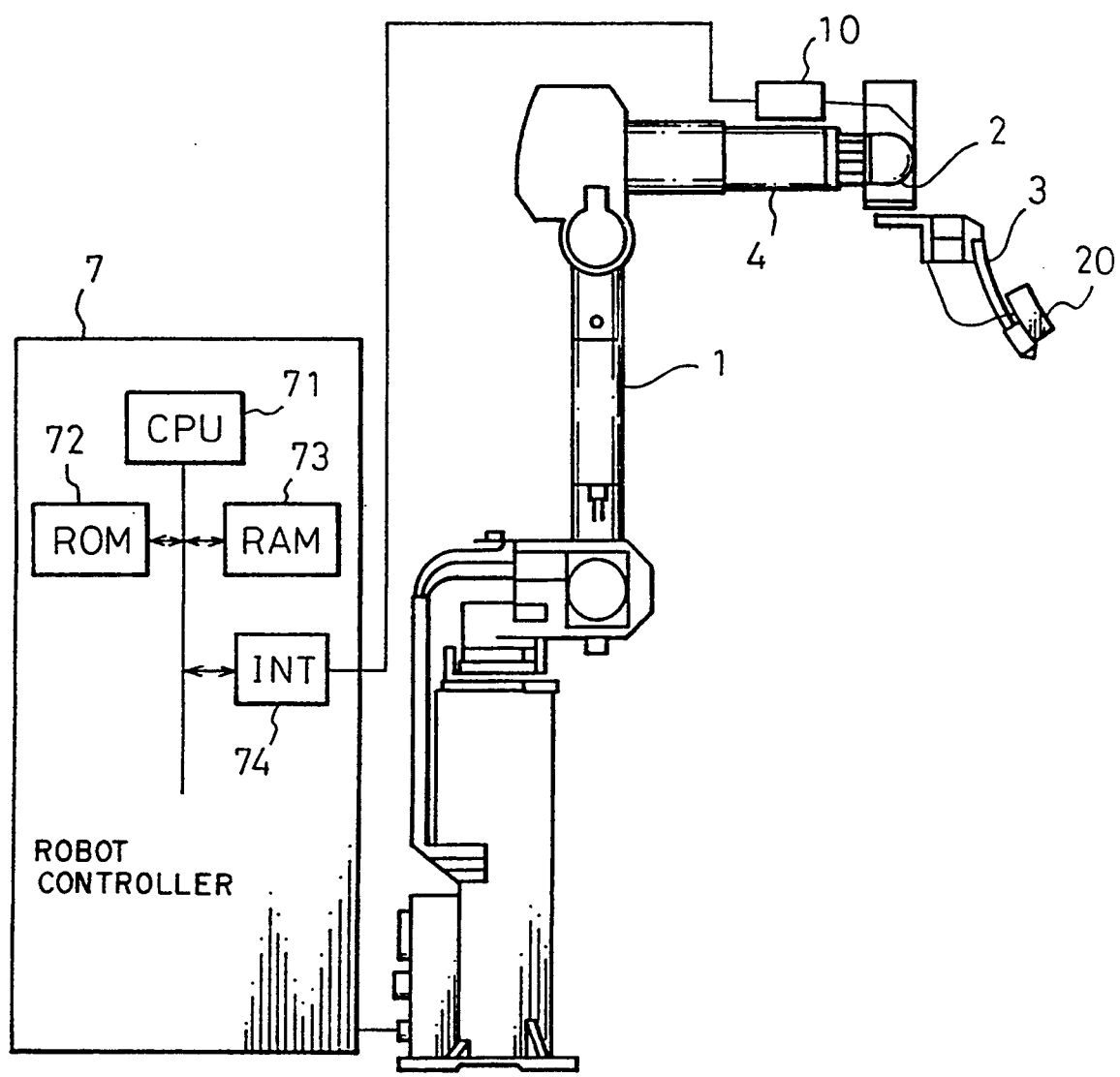
FIG. 2 is an outline drawing of an arc welding robot.

FIG. 2 is an outline drawing of an arc welding robot. A torch 3 is connected at the tip of a hand 2 of a robot 1. The arc sensor unit 20 is provided with the torch 3. The arc sensor control unit 10 is also provided at an arm 4. The arc sensor control unit 10 controls the behavior of the arc sensor unit 20 in accordance with con, hand signals output from the robot controller 7. The robot controller 7 is mainly composed of a processor 71. The processor 71 outputs the con, hand signals in accordance with a system program stored in a ROM 72, and controls the robot 1 and the arc sensor control unit 10.

In the ROM 72, a system program for controlling the robot behavior, a system program for controlling the arc sensor control unit 10 and a program for the process of the apparatus for monitoring the guard window of the arc sensor, hereinafter explained, are stored.

In a RAM 73, a program for processing the operations of the robot 1, system parameters, data necessary for the arc sensor, data on the quantity of light reception detected by the apparatus for monitoring, and data involving the average value of the same are stored.

Next, operations of the apparatus for monitoring the guard window of the arc sensor will be explained hereinafter.

First of all, after mounting an unused (brand new) guard window 28 of an arc sensor to the arc sensor unit 20, a standard light reflecting plate 30 is located at a position a determined distance from a front surface of the guard window 28. The standard reflecting plate 30 has a standard surface of which roughness and reflection rate are uniform, for example, the plate 30 is composed of a plaster board so that a uniform irregular reflection can be obtained when the laser beam 26 is projected. The reflected light 27 is detected by the light receptive element 25 after penetrating the lens 24 when the laser beam 26 is projected to the standard reflecting plate 30. Data obtained by the detection are sent to the robot controller 7 via the signal detecting unit 13 of the arc sensor control unit 10, and are input via an interface 74. The detected input data are stored in the RAM 73. The laser beam 26 scans the whole scanning surface area of the standard reflecting plate 30, and the whole detected data are stored at the RAM 73. The average value of all the detected data is calculated and also stored in the RAM 73.

Next, after arc welding while maintaining the guard window 28 of the arc sensor mounted at the arc sensor unit 20 as it is, the standard reflecting plate 30 is located at a position a determined distance from the front surface of the guard window 28 as in the above explained case. The laser beam 26 is projected to the standard reflecting plate 30, and detected data of the reflected light 27 are then sent to the robot controller 7 as in the above explained case.

The processor 71 of the robot controller 7 compares the sent detected data with the detected data previously memorized before the guard window 28 is used for welding, and determines whether the detected data sent exceeds a determined level or not. This level is determined, for example, based on the calculated differences between the two detected data, and when the difference is large, the processor 71 judges that there is a stain or lampblack generated by the spatterings on the surface of the guard window 28 through which the laser beam 26 passes when the quantities of light reception are detected.

The result of the judgement is displayed as a message so that operators can discern that the guard window 28 is partly stained. On the other hand, when the difference is small, the processor 71 determines that there are not stains or otherwise on the guard window 28 and that the window 28 does not require replacement.

When the laser beam 26 scans the whole standard reflecting surface 30 and the detected data are obtained, the average value of the whole detected data is also calculated. This average value is compared with the previously stored average value of the detected data detected before the guard window 28 is used for an arc welding operation. When the difference between the two average values is large, the processor 71 determines that there are stains on the guard window 28 by the lampblack, and the result of the determination is displayed as a message, and the operator discerns that there are stains or otherwise on the whole guard window 28 of the arc sensor based on the display. On the other hand, when the difference is small, the processor 71 discerns that there are no stains on the whole guard window 28.

Figure 3:
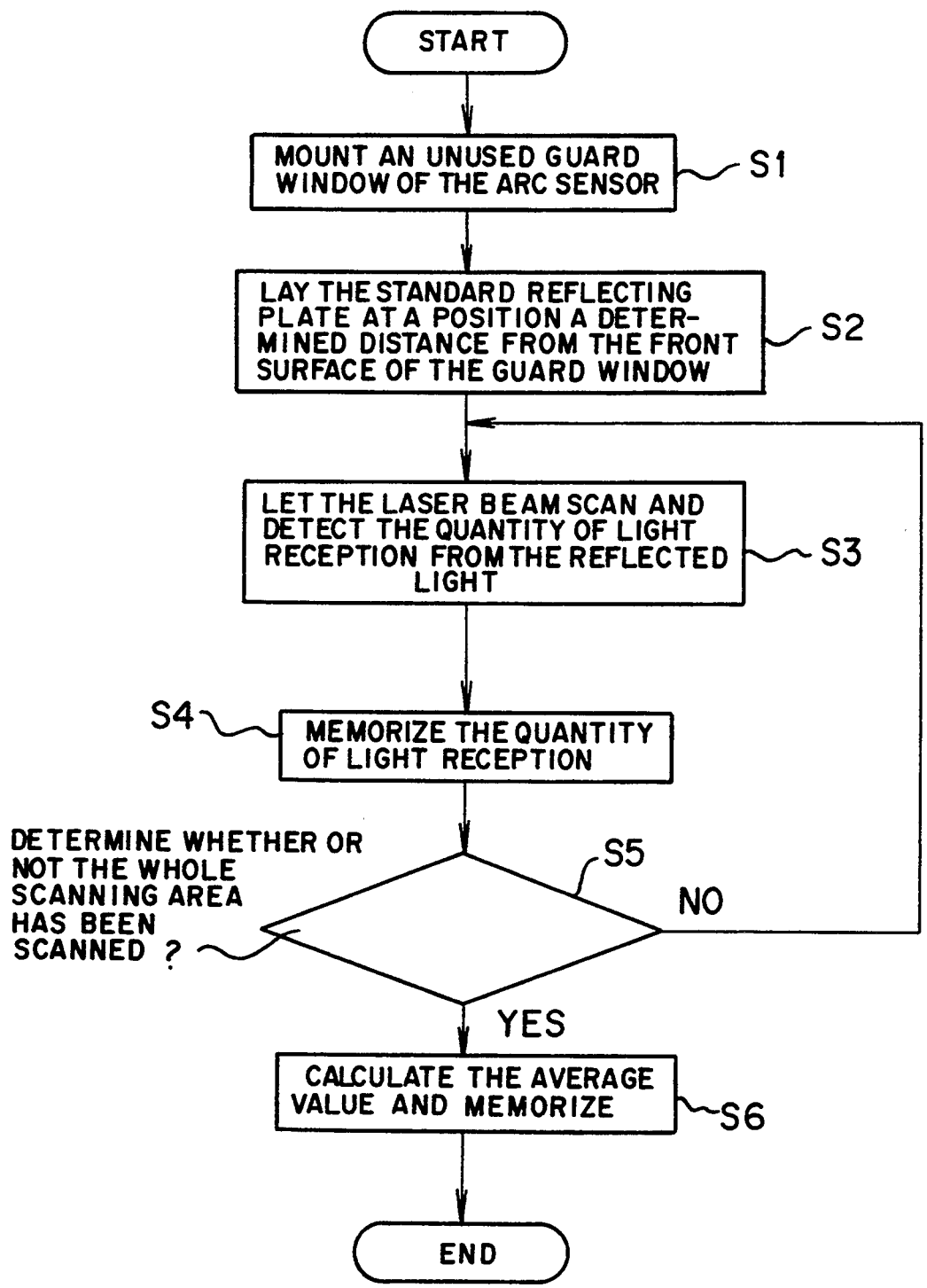
FIG. 3 is a flow chart of a process for the apparatus (for monitoring a guard window of an arc sensor of the present invention) before the guard window is used for welding operation; and, FIG. 4 is a flow chart of a process for determining the replacement time of the guard window of the apparatus.
Figure 4:
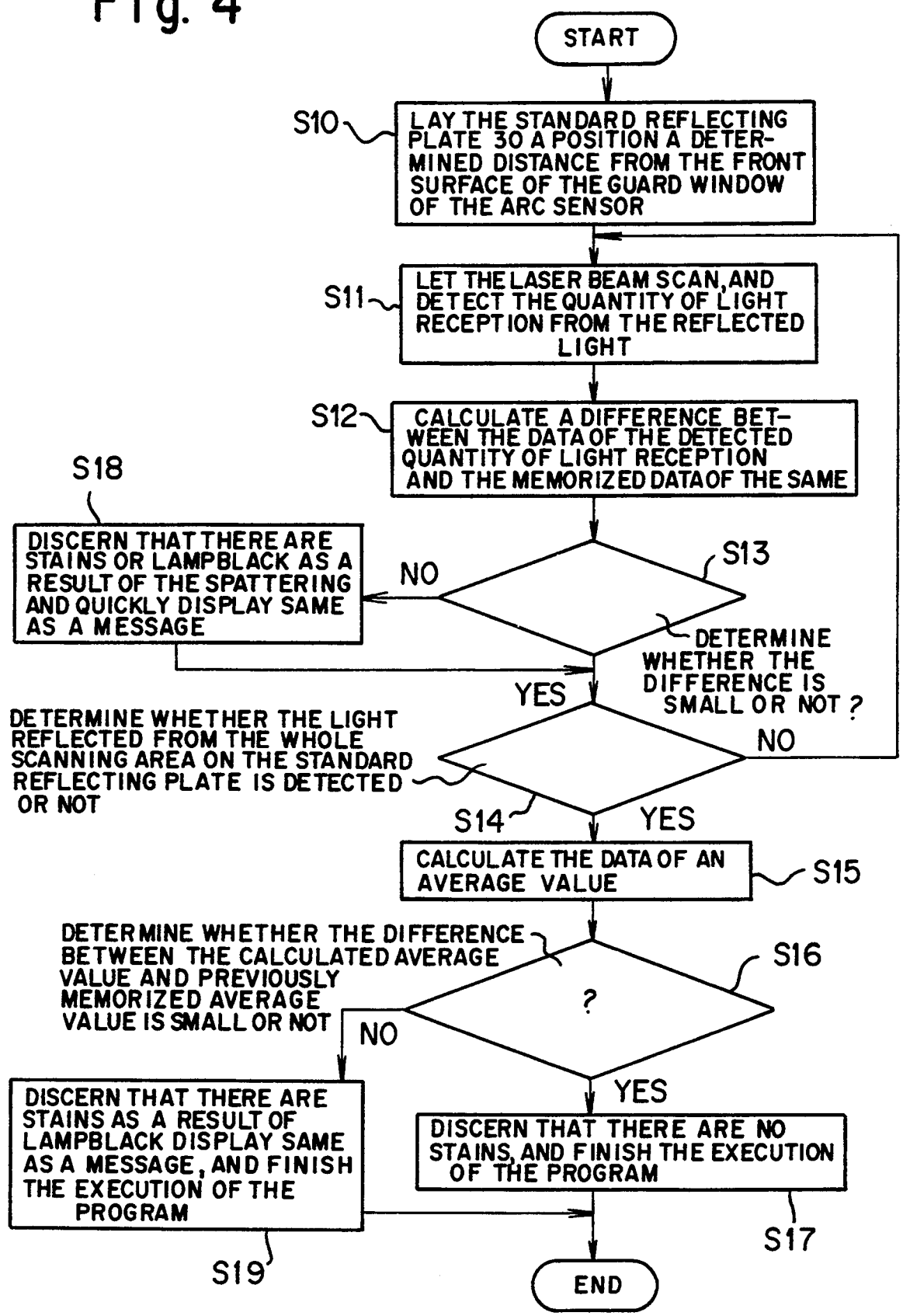

FIG. 3 and FIG. 4 are flow charts of a process for the apparatus for monitoring a guard window of an arc sensor of the present invention. In the drawings, the numbers following after alphabet "s" indicate step numbers.

FIG. 3 shows a process flow chart of the apparatus before the guard window of the arc sensor is used for arc welding, whereas a process flow chart of the same shown in FIG. 4 is based on the detected data before the guard window is used for an arc welding operation.

(S1): Mount an unused guard window 28 of the arc sensor in the arc sensor unit 20.

(S2): Lay the standard reflecting plate 30 at a position a determined distance from the front surface of the guard window 28.

(S3): Let the laser beam 26 scan on the standard reflecting plate 30, and detect the quantity of light reception from the reflected light 27.

(S4): Memorize the quantity of light reception.

(S5): Determine whether or not the whole scanning area on the standard reflecting plate 30 has been scanned and detected. If the whole area has been scanned and detected, go to step S6, and if not, go back to step S3.

(S6): Calculate the average value of the quantity of the reflected light reception from the whole scanning area on the standard reflecting plate 30, and memorize the calculated data.

FIG. 4 is a flow chart of a process for determining the replacement time of the guard window of the apparatus after arc welding, with the guard window used in the process explained by referring to FIG. 3.

(S10): Lay the standard reflecting plate 30 at a position a determined distance from the front surface of the guard window 28 of the arc sensor.

(S11): Let the laser beam 26 scan, and detect the quantity of light reception from the reflected light 27.

(S12): Calculate a difference between the data of the detected quantity of light reception and the memorized data of the same stored before the guard window is used for an arc welding operation.

(S13): Determine whether the difference is small or not, and if it is small, go to step S14, and if it is large, go to step S18 respectively.

(S14): Determine whether the light reflected from the whole scanning area on the standard reflecting plate 30 is detected or not. If it is detected, go to step S15, and if not, go back to step S11.

(S15): Calculate the data of an average value of the quantity of light reception detected for the whole scanning area.

(S16): Determine whether the difference between the calculated average value and previously memorized average value of the quantity of light reception detected before using the guard window is small or not, and if it is determined to be small, go to step S17, and if it is determined to be large, go to step S19, respectively.

(S17): Discern that there are no stains or otherwise on the guard window 28 of the arc sensor, thereby determining that the guard window is normal, and finish the execution of the program.

(S18): Discern that there are stains or lampblack as a result of the spatterings on the guard window 28 of the arc sensor when it is detected, quickly display same as a message, and go to step S14.

(S19): Discern that there are stains or otherwise as a result of lampblack on the whole area of the guard window 28, display same as a message, and finish the execution of the program.

In this way, the quantity of light reception detected before using the guard window 28 for an arc welding operation is compared with the same detected after using it for an arc welding operation, and the condition of the guard window is determined based on the results of the comparison, and the replacement time of the guard window is determined. By this, the replacement time of the guard window 28 can be properly determined using an original function of the arc sensor; the function of which detects the quantity of light reception from the reflected light. Therefore, a suitable replacement time of the guard window 28 of the arc sensor can be determined. If said process is executed at the beginning of every arc welding operation, the replacement time of the guard window can be accurately determined.

As explained above, an apparatus for monitoring a guard window of an arc sensor according to the present invention compares the quantity of detected light reception before using the guard window for an arc welding operation with the quantity of detected light reception after using the guard window for an arc welding operation discerns the condition of the guard window of the arc sensor, and determines whether it is acceptable or not based on the result of the said comparison, and determines the replacement time of the guard window.

Therefore, the proper replacement time of the guard window can be determined using an original function of the arc sensor, which detects the quantity of light reception from the reflected light, so that the guard window can be replaced at an appropriate time.

We claim:

1. A welding robot apparatus including guard window monitoring apparatus for an arc sensor guard window (28) of the robot, said apparatus comprising:

robot controller means (7);

an arc sensor unit (20) having laser scanner means (22) controlled by arc sensor control means (10) for directing a laser beam to scan a welding area for determining a welding point of work, said arc sensor unit (20) including a light receptive element (25) providing signals to signal detecting means (13) representing intensity of reflected light from an object being worked to determine said welding point;

a standard reflecting plate (30) located at a position a determined distance from a front surface of said guard window (28) at a side of said guard window (28) opposite from a position of said light receptive element (25);

means in said controller means (7) selectively operable to cause said laser scanner means (22) to direct said laser beam to scan a surface of said standard reflecting plate (30) through said guard window (28) such that said light receptive element (25) provides a signal to said signal detecting means (13) representing a first quality of light reflected from a scanning area of said standard reflecting plate (30) through said guard window (28) before using said guard window (28) for an arc welding operation and provides a signal to said signal detecting means (13) representing a second quantity of light reflecting from the scanning area of said standard reflecting plate (30) after using said guard window (28) for an arc welding operation; and means in said robot controller means (7) for storing signals from said signal detecting means (13) representative of said first and second quantities of light, and for determining a replacement time of said guard window based upon a comparison between signals representing said first quantity of light and said second quantity of light to determine a magnitude of difference therebetween.

2. An apparatus as recited in claim 1, wherein said replacement time determination is made by comparison of signals representing first and second quantities of light corresponding to light reflecting from a portion of the scanning area of said standard reflecting plate (30).

3. An apparatus as recited in claim 1, wherein said replacement time determination is made by a comparison of signals representing average values of said first quantity of light and said second quantity of light reflected from the whole scanning area of said standard reflecting plate (30).

* * * * *